(12) United States Patent
Tupman

(10) Patent No.: US 8,585,979 B2
(45) Date of Patent: Nov. 19, 2013

(54) ENHANCED PHOTO-CATALYTIC CELLS

(75) Inventor: David Tupman, Anna, TX (US)

(73) Assignee: Puradigm, LLC, Las Vegas, NV (US)

( * ) Notice: Subject to any disclaimer, the term of this patent is extended or adjusted under 35 U.S.C. 154(b) by 0 days.

(21) Appl. No.: 13/115,546

(22) Filed: May 25, 2011

(65) Prior Publication Data
US 2012/0058006 A1 Mar. 8, 2012

Related U.S. Application Data

(60) Provisional application No. 61/380,462, filed on Sep. 7, 2010.

(51) Int. Cl.
A62B 7/08 (2006.01)

(52) U.S. Cl.
USPC .......................... 422/122; 422/121

(58) Field of Classification Search
USPC ................................ 422/121, 122
See application file for complete search history.

(56) References Cited

U.S. PATENT DOCUMENTS

| | | | |
|---|---|---|---|
| 3,607,133 A | 9/1971 | Hirao et al. | |
| 4,230,571 A | 10/1980 | Dadd | |
| 5,078,971 A | 1/1992 | Matuda et al. | |
| 6,074,981 A | 6/2000 | Tada et al. | |
| 6,139,803 A | 10/2000 | Watanabe et al. | |
| 6,149,717 A | 11/2000 | Satyapal | |
| 6,194,346 B1 | 2/2001 | Tada et al. | |
| 6,221,314 B1 * | 4/2001 | Bigelow | 422/24 |
| 6,280,806 B1 | 8/2001 | Park et al. | |
| 6,391,269 B1 | 5/2002 | Yoshimatu | |
| 6,500,387 B1 * | 12/2002 | Bigelow | 422/24 |
| 6,524,536 B2 | 2/2003 | Newman et al. | |
| 6,558,639 B1 | 5/2003 | Watanabe et al. | |
| 6,752,957 B1 | 6/2004 | De Lasa et al. | |
| 6,794,065 B1 | 9/2004 | Morikawa et al. | |
| 6,902,653 B2 | 6/2005 | Carmignani et al. | |
| 7,264,657 B2 | 9/2007 | Yuen | |
| 7,329,313 B2 | 2/2008 | Wu | |
| 7,371,351 B2 | 5/2008 | Goswami | |
| 7,520,978 B2 | 4/2009 | Harbers | |
| 7,704,913 B2 | 4/2010 | Tani et al. | |
| 7,758,821 B2 | 7/2010 | Reisfeld et al. | |
| 7,763,206 B2 | 7/2010 | Mole | |

(Continued)

FOREIGN PATENT DOCUMENTS

| | | |
|---|---|---|
| JP | 11276558 A | 10/1999 |
| JP | 2000254452 A | 9/2000 |

(Continued)

OTHER PUBLICATIONS

Intech Marketing, "Theairpurifiers.com," AirPura Air Purifier Design, Jan. 1, 2009, pp. 1-2.

(Continued)

Primary Examiner — Kevin Joyner
(74) Attorney, Agent, or Firm — McAndrews, Held & Malloy, Ltd.

(57) ABSTRACT

A photo-catalytic cell may produce bactericidal molecules in air by passing air across catalyst coated targets. Ultraviolet (UV) energy may be emitted from a source. A first portion of the UV energy from the source may be applied directly onto the targets. A second portion of the UV energy from the source may be reflected onto the targets.

7 Claims, 2 Drawing Sheets

(56) References Cited

U.S. PATENT DOCUMENTS

Figure 1:
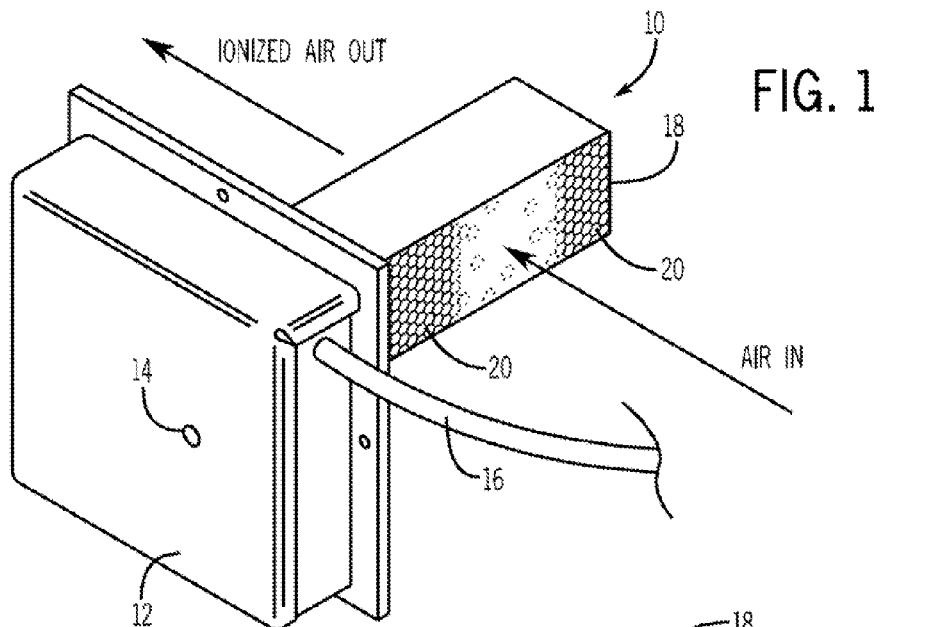
Figure 3:
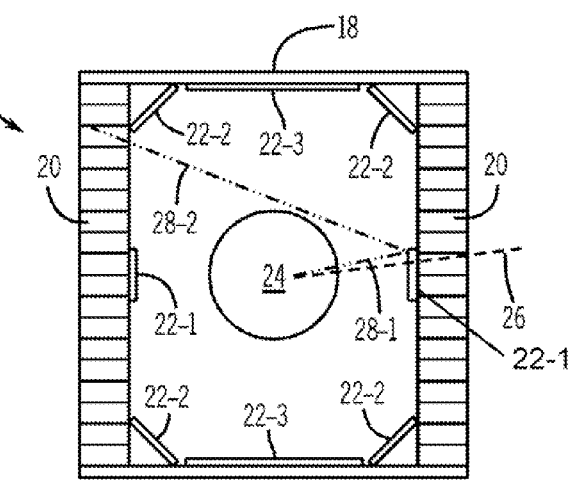
Figure 2:
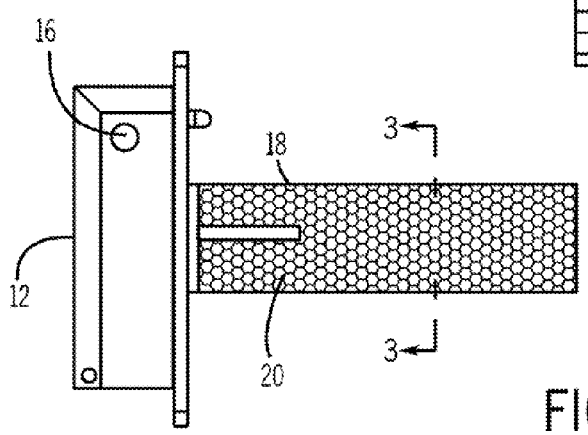
Figure 4:
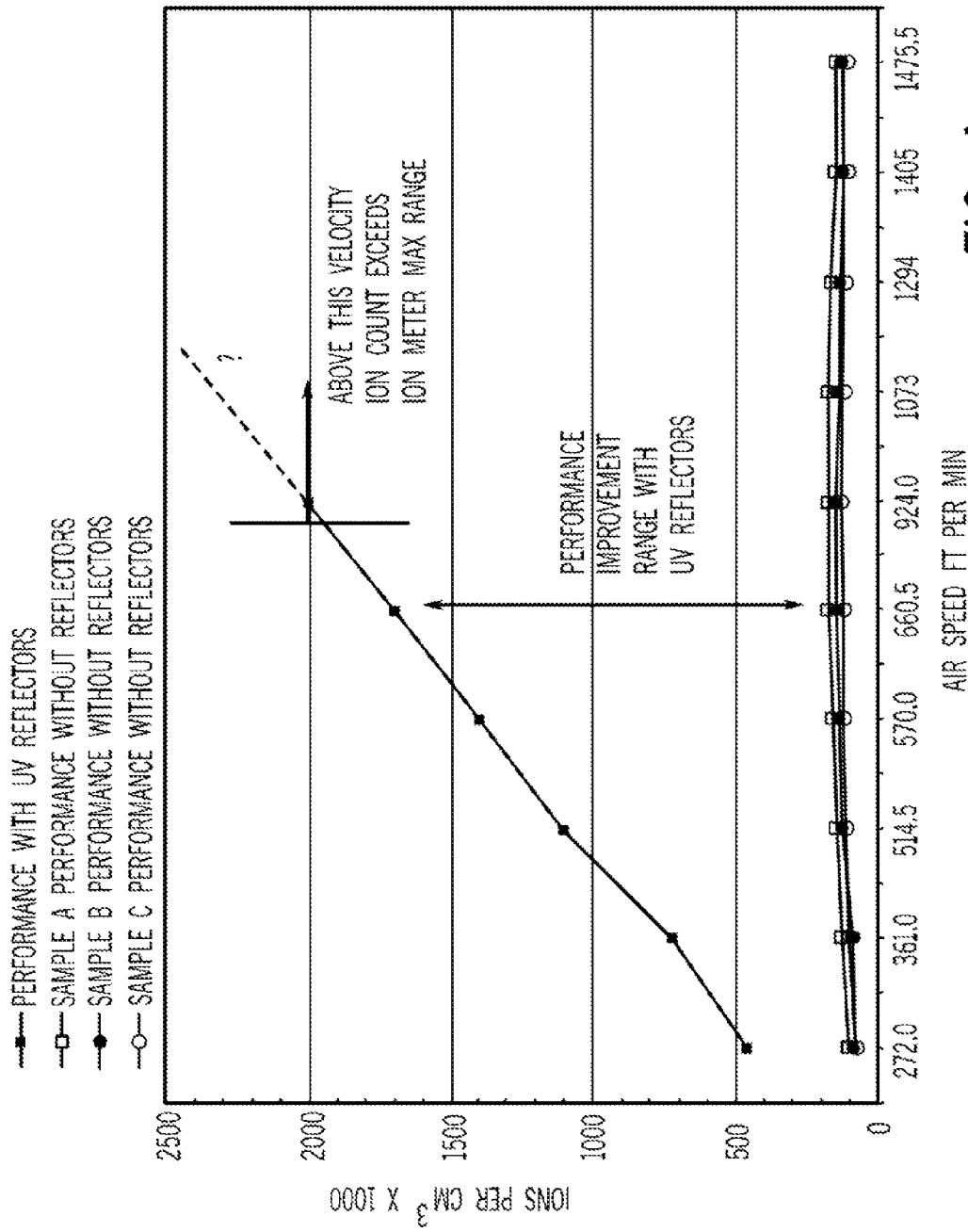

| | | |
|---|---|---|
| 7,820,100 B2 | 10/2010 | Garfield et al. |
| 7,824,626 B2 | 11/2010 | Kwiatkowski |
| 8,012,412 B2 | 9/2011 | Normark et al. |
| 2002/0094298 A1 | 7/2002 | Monagan |
| 2003/0211022 A1 | 11/2003 | Gross et al. |
| 2004/0013583 A1 | 1/2004 | Burkhardt |
| 2004/0069940 A1* | 4/2004 | Brown ..................... 250/237 R |
| 2004/0248075 A1 | 12/2004 | Yamaguchi et al. |
| 2005/0061656 A1 | 3/2005 | Benoit et al. |
| 2005/0063881 A1 | 3/2005 | Senne et al. |
| 2005/0186124 A1 | 8/2005 | Fink et al. |
| 2005/0191205 A1 | 9/2005 | Uslenghi et al. |
| 2005/0201907 A1 | 9/2005 | Wakamura |
| 2005/0220680 A1 | 10/2005 | Ma et al. |
| 2007/0194255 A1 | 8/2007 | Garcia et al. |
| 2007/0251812 A1 | 11/2007 | Hayman et al. |
| 2008/0031783 A1 | 2/2008 | Briggs et al. |
| 2008/0112845 A1 | 5/2008 | Dunn |
| 2008/0170971 A1 | 7/2008 | Bergeron et al. |
| 2008/0253941 A1 | 10/2008 | Wichers et al. |
| 2009/0035176 A1 | 2/2009 | Normark et al. |
| 2009/0152096 A1 | 6/2009 | Carlson |
| 2009/0166282 A1 | 7/2009 | Dong |
| 2009/0191100 A1 | 7/2009 | Deal |
| 2010/0092346 A1 | 4/2010 | Jeon |
| 2010/0143205 A1 | 6/2010 | Engelhard |
| 2010/0202932 A1 | 8/2010 | Danville |
| 2010/0266445 A1* | 10/2010 | Campagna ..................... 422/23 |
| 2010/0303679 A1 | 12/2010 | Kim |
| 2012/0058006 A1 | 3/2012 | Tupman |

FOREIGN PATENT DOCUMENTS

| | | |
|---|---|---|
| JP | 2001061947 A | 3/2001 |
| JP | 2001-299881 A | 10/2001 |
| JP | 2001340441 A | 12/2001 |
| JP | 2004333035 A | 11/2004 |
| JP | 2005152708 A | 6/2005 |
| JP | 2005198846 A | 7/2005 |
| JP | 2005-343427 A | 12/2005 |

OTHER PUBLICATIONS

Country Air, LLC, "Air Purifiers," Saver APR Object Cleaner, Jul. 2011, pp. 1-2.
ActivTek product brochure (copy attached).
GreenTech product brochure (copy attached).
RGF probe product brochure (copy attached).
International Search Report and the Written Opinion, 11 pages, Jan. 23, 2012.
International Search Report and Written Opinion in International application No. PCT/US2012/053831, dated Feb. 25, 2013. (13 pages).

\* cited by examiner

ENHANCED PHOTO-CATALYTIC CELLS

RELATED APPLICATIONS

This application claims the benefit of U.S. Provisional Patent Application 61/380,462 filed on Sep. 7, 2010.

BACKGROUND OF THE INVENTION

The present invention generally relates to methods and apparatus for producing an enhanced ionized cloud of bactericidal molecules.

Photo-catalytic cells may be employed to produce bactericidal molecules in air flow passing through the cells. The cells may be positioned to ionize air that may then be directed into an enclosed space or room. Emerging molecules from the cells may have a bactericidal effect on various bacteria, molds or viruses which may be airborne in the room or may be on surfaces of walls or objects in the room.

Typically, such cells may be constructed with a "target material" (or coated surface(s) surrounding a broad spectrum ultraviolet (UV) emitter. This combination can produce an ionized cloud of bactericidal molecules. The target may be coated with titanium dioxide as well as a few other proprietary trace elements. As air passes through or onto the target, UV energy striking the titanium dioxide may result in a catalytic reaction that may produce the desired cloud of bactericidal molecules within the airflow. These molecules, upon contact with any bacteria, mold or virus, may kill them.

Effectiveness of such photo-catalytic cells may be dependent on the concentration of the bactericidal molecules which may be produced by the cells. The bactericide concentration level may be dependent on the degree to which UV energy is applied to the titanium dioxide of the honeycomb mesh.

As can be seen, there is a need for a system in which a higher proportion of UV energy from a UV emitter (in such a photo-catalytic cell) can be caused to impinge upon the titanium dioxide within the cell.

SUMMARY OF THE INVENTION

In one aspect of the present invention, a photo-catalytic cell with an ultraviolet (UV) emitter and catalyst-coated targets may be comprised of at least one UV reflector configured to reflect UV energy from the UV emitter onto the targets. The rectangular "honeycomb matrix" target shape shown in the attached FIGS. 1, 2 and 3 is just one of many mechanical shapes that could use the proposed "enhanced ionization" technology proposed in this application. The proposed enhancement technology consist of reflective surfaces that have the unique reflective specifications as described in paragraphs 21 thru 26.

In another aspect of the present invention, a method for producing bactericidal molecules in air may comprise the steps of: passing air across catalyst coated targets; emitting UV energy from a source; applying a first portion of the UV energy from the source directly onto the targets; and reflecting a second portion of the UV energy from the source onto the targets.

These and other features, aspects and advantages of the present invention will become better understood with reference to the following drawings, description and claims.

BRIEF DESCRIPTION OF THE DRAWINGS

FIG. 1 is a perspective view of a typical photo-catalytic cell in accordance with an embodiment of the invention in which a typical "honeycomb matrix" is shown as the "target";

FIG. 2 is a side elevation view of the photo-catalytic cell of FIG. 1;

FIG. 3 is a cross sectional view of the photo-catalytic cell of FIG. 2 taken along the line 3-3; and FIG. 4 is a comparison graph showing a difference in performance of the photo-catalytic cell of FIG. 1 with and without use of UV reflectors in accordance with the invention.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, embodiments of the present invention generally provide photo-catalytic cells in which reflectors may be positioned to reflect UV energy and increase a proportion of emitted UV energy that strikes titanium dioxide in the cell at high incident angles.

Referring now to the Figures, it may be seen that an exemplary embodiment of a photo-catalytic cell 10 may comprise an electronics box 12; a light pipe indicator 14; a power cord 16; a chamber 18; honeycomb targets 20; UV reflectors 22-1, 22-2 and 22-3; and a UV emitter or lamp 24. The honeycomb targets 20 may be coated with titanium dioxide.

In operation, air may pass across the honeycomb targets 20 while UV energy may be applied to the target 20 by the lamp 24. A photo-catalytic reaction may take place in the presence of the UV energy. The reaction may produce bactericidal molecules in the air.

Referring now particularly to FIG. 3, the efficacy of the UV reflectors 22-1 may be illustrated. If the reflector 22-1 were not present, an emitted ray 26 might pass through the honeycomb target 20 without impinging on the titanium dioxide. However, when one of the reflectors 22-1 is present, an illustrative emitted ray 28-1 of UV energy may impinge on the UV reflectors 22-1. The ray 28-1 may be reflected to become a reflected ray 28-2. It may be seen that the reflected ray 28-2 may impinge on a surface of the honeycomb target 20. It may be seen that a hypothetical unreflected ray 26, which might follow a path parallel to that of the ray 28-1, might pass through the honeycomb target 20 without impinging on the target 20. Thus, presence of the reflector 22-1 in the path of the ray 28-1 may result in avoidance of loss of the UV energy from the ray 28-1. The reflectors 22-1 may be relatively small as compared to the size of the honeycomb target 20. The small size (about 10% of the size of the target 20) may allow for minimal air flow obstruction. In spite of their relatively small size, the reflectors 22-1 may be effective because they may reflect virtually all of the (normally lost) UV energy that is emitted in a direction that is almost orthogonal (i.e., within ±5° of orthogonality) to the outer vertical plane of the honeycomb target 20. Hence, UV energy would pass thru the honeycomb target without touching the TiO2 surface. But by "reflecting" the UV rays onto the "opposite side" target matrix—that energy could be captured and utilized so as to add to the total ion count within the desired cloud of ionized molecules. In other words, the number of ions created by any incoming UV ray is proportional to the sine of the incident angle (Theta) between the UV ray path and the TiO2 surface that a given ray is impacting.

| At theta = 90 deg | Sine (90) = 1 | Maximum energy gathered |
|---|---|---|
| At theta = 0 deg | Sine (0) = 0 | Minimum energy gathered |

Reflectors 22-3 may be interposed between the lamp 24 and walls of the chamber 18. UV energy striking the reflectors 22-3 may be reflected onto the honeycomb target 20. Thus presence of the reflectors 22-3 may result in avoidance of loss of UV energy that might otherwise be absorbed or diffused by walls of the chamber 18. Similarly, reflectors 22-2 may be placed in corners of the chamber 18 to reflect UV energy onto the honeycomb target 20.

The reflectors 22-1, 22-2 and/or 22-3 may be constructed from material that is effective for reflection of energy with a wavelength in the UV range (i.e., about 184 nanometers [nm] to about 255 nm). While soft metals such as gold and silver surfaces may be effective reflectors for visible light, their large grain size may make them less suitable than metallic surfaces with a small grain size (i.e., hard metals). Thus, hard metals such as chromium and stainless steel and other metals that do not readily oxidize may be effective UV reflectors and may be particularly effective for use as UV reflectors in the photo-catalytic cell 10. Material with a UV reflectivity of about 90% or higher may be suitable for use in the reflectors 22-1, 22-1 and 22-3. Lower reflectively produces lower effectiveness. To achieve the level of reflection required, it may be necessary to "micro-polish or buff" a selected materials reflective surface to achieve the specifications defined in para 22]-24] below.

Advantageously, reflecting surfaces of the reflectors 22 should be electrically conductive. Specifically, outer surface coatings (added for oxidation protection) like glass, clear plastics, clear anodization (i.e. non-conductive) may diminish (considerably) any performance enhancement of the photo-catalytic cell 10.

Also it is important that reflecting surfaces of the UV reflector 22 produce surface specular reflection. (Specular reflection being a "mirror-like reflection" of light—in which a single incoming light ray is reflected into a single outgoing direction) Specular reflection is distinct from "diffuse" reflection where an incoming light ray is reflected into a broad range of directions. Diffuse reflection may diminish performance enhancement of the photo-catalytic cell 10.

In an exemplary embodiment of the photo-catalytic cell 10, the reflectors 22-1, 22-2 and 22-3 may be chromium-plated plastic. Chromium-plated plastic may be a desirably low cost material with a desirably high degree of reflectivity for UV energy. So called "soft chrome" such as the plating used to produce a mirror-like finish that is seen on automobile chromed surfaces may be advantageously employed.

It may be noted that there may be other cell shape designs which are not rectangular. For example, the cell 10 may be circular, tubular, or may have an otherwise complex shape. For these non-rectangular shaped cells, an optimum reflector design may be curved or otherwise non-flat in shape.

It should be understood, of course, that the foregoing relates to exemplary embodiments of the invention and that modifications may be made without departing from the spirit and scope of the invention as set forth in the following claims.

What is claimed is:

1. An apparatus for ionizing air, the apparatus comprising:
a chamber including:
a top portion,
a bottom portion,
a first side including a first target comprising:
a plurality of passages between an interior area of the chamber and an exterior area of the chamber, and
a photo-catalytic coating on the plurality of passages;
a second side opposite the first side and including a second target comprising:
a plurality of passages between the interior area of the chamber and the exterior area of the chamber, and
the photo-catalytic coating on the plurality of passages;
a first reflector arranged on the top portion of the chamber and configured to:
reflect UV energy emitted along a dimension towards the first target from a UV emitter located within the chamber directly to the photo-catalytic coating of the first target, wherein the first reflector is a specular UV reflector, and
reflect UV energy emitted along a dimension towards the second target from the UV emitter directly to the photo-catalytic coating of the second target;
a second reflector arranged on the bottom portion of the chamber and configured to:
reflect UV energy emitted along a dimension towards the first target from the UV emitter located within the chamber directly to the photo-catalytic coating of the first target, wherein the second reflector is a specular UV reflector, and
reflect UV energy emitted along a dimension towards the second target from the UV emitter directly to the photo-catalytic coating of the second target; and
wherein the photo-catalytic coating is arranged to:
receive UV energy directly from the UV emitter,
receive UV energy reflected from the first reflector, and
receive UV energy reflected from the second reflector.

2. The apparatus of claim 1, further comprising at least one corner reflector arranged in an interior corner of the chamber, wherein the at least one corner reflector is a specular UV reflector.

3. The apparatus of claim 1, further comprising:
a third reflector located at a corner between the first target and the first reflector;
a fourth reflector located at a corner between the second target and the first reflector;
a fifth reflector located at a corner between the first target and the second reflector; and
a sixth reflector located at a corner between the first target and the second reflector.

4. The apparatus of claim 1, further comprising an additional reflector on the first target and facing the interior area of the chamber,
wherein the additional reflector configured to reflect UV energy that is emitted from the UV emitter in a direction that is almost orthogonal to the first target, and
wherein the additional reflector is a specular UV reflector.

5. The apparatus of claim 1, wherein a reflecting surface of the first reflector is electrically conductive.

6. The apparatus of claim 1, wherein the first target comprises a honeycomb matrix.

7. The apparatus of claim 1, wherein the first reflector comprises a material having a UV reflectivity of about 90% or greater at UV wavelengths of 185 nm and 254 nm.

* * * * *